US012558150B2

(12) United States Patent (10) Patent No.: US 12,558,150 B2
Sanker et al. (45) Date of Patent: Feb. 24, 2026

(54) INTEGRATED SENSORS FOR ENERGY TOOLS

(71) Applicant: Verb Surgical Inc., Santa Clara, CA (US)

(72) Inventors: Benjamin Alan Sanker, San Jose, CA (US); Berk Gonenc, San Jose, CA (US); Jose Luis Cordoba, Malaga (ES); Pablo Garcia Kilroy, Menlo Park, CA (US)

(73) Assignee: Verb Surgical Inc., Santa Clara, CA (US)

(*) Notice: Subject to any disclaimer, the term of this patent is extended or adjusted under 35 U.S.C. 154(b) by 722 days.

(21) Appl. No.: 17/504,879

(22) Filed: Oct. 19, 2021

(65) Prior Publication Data

US 2023/0121554 A1 Apr. 20, 2023

(51) Int. Cl.
*A61B 18/14* (2006.01)
*A61B 18/00* (2006.01)

(52) U.S. Cl.
CPC ...... *A61B 18/1445* (2013.01); *A61B 18/1482* (2013.01); *A61B 2018/00577* (2013.01); *A61B 2018/00589* (2013.01); *A61B 2018/00595* (2013.01); *A61B 2018/00601* (2013.01); *A61B 2018/0063* (2013.01); *A61B 2018/00702* (2013.01); *A61B 2018/00791* (2013.01)

(58) Field of Classification Search
CPC ............ A61B 18/1442; A61B 18/1445; A61B 18/1447; A61B 2018/1442; A61B 2018/145; A61B 2018/1452; A61B 2018/1455; A61B 2018/1457; A61B 2018/146; A61B 2018/1462

See application file for complete search history.

(56) References Cited

U.S. PATENT DOCUMENTS

| | | | |
|---|---|---|---|
| 4,719,538 A | 1/1988 | Cox | |
| 4,793,429 A | 12/1988 | Bratton et al. | |
| 4,951,510 A | 8/1990 | Holm-Kennedy et al. | |
| 5,345,824 A | 9/1994 | Sherman et al. | |
| 5,436,795 A | 7/1995 | Bishop et al. | |
| 5,492,020 A | 2/1996 | Okada | |

(Continued)

FOREIGN PATENT DOCUMENTS

| | | |
|---|---|---|
| EP | 2904984 A1 | 8/2015 |
| EP | 3298974 A1 | 3/2018 |

(Continued)

OTHER PUBLICATIONS

PCT/IB2022/058650, "PCT Notification of Transmittal of the International Search Report and the Written Opinion of the International Searching Authority, or the Declaration", mailed Dec. 27, 2022, 11 pages.

(Continued)

*Primary Examiner* — Joanne M Rodden
*Assistant Examiner* — Alyssa M Pape
(74) *Attorney, Agent, or Firm* — Aikin & Gallant, LLP

(57) ABSTRACT

An energy tool for a surgical robotic system, the energy tool comprising: a jaw coupled to a base, the jaw having a first anvil that moves relative to a second anvil between an open position and a closed position; and at least one of a force sensor, a temperature sensor and an acoustic sensor coupled to the jaw.

11 Claims, 13 Drawing Sheets

(56) References Cited

U.S. PATENT DOCUMENTS

| | | | |
|---|---|---|---|
| 5,561,247 A | 10/1996 | Mutoh et al. | |
| 5,576,483 A | 11/1996 | Bonin | |
| 5,661,235 A | 8/1997 | Bonin | |
| 6,159,761 A | 12/2000 | Okada | |
| 8,596,111 B2 | 12/2013 | Dargahi et al. | |
| 8,893,946 B2 | 11/2014 | Boudreaux et al. | |
| 10,555,790 B2 | 2/2020 | Paul et al. | |
| 10,876,907 B2 | 12/2020 | Yoon et al. | |
| 11,060,927 B2 | 7/2021 | O'Connell et al. | |
| 11,100,631 B2 | 8/2021 | Yates et al. | |
| 11,864,726 B2* | 1/2024 | Batchelor | A61B 18/1445 |
| 2002/0039271 A1 | 4/2002 | Fournier et al. | |
| 2002/0149571 A1 | 10/2002 | Roberts | |
| 2003/0036214 A1 | 2/2003 | Eskridge | |
| 2004/0116952 A1 | 6/2004 | Sakurai et al. | |
| 2004/0237650 A1 | 12/2004 | Yang | |
| 2005/0131390 A1 | 6/2005 | Heinrich et al. | |
| 2005/0229710 A1 | 10/2005 | O'Dowd et al. | |
| 2007/0043725 A1 | 2/2007 | Hotelling | |
| 2007/0179408 A1 | 8/2007 | Soltz | |
| 2007/0205776 A1 | 9/2007 | Harish et al. | |
| 2007/0227257 A1 | 10/2007 | Harish et al. | |
| 2008/0087105 A1 | 4/2008 | Renken et al. | |
| 2008/0296346 A1 | 12/2008 | Shelton et al. | |
| 2008/0300580 A1 | 12/2008 | Shelton, IV | |
| 2009/0033078 A1 | 2/2009 | Hawes et al. | |
| 2009/0065267 A1 | 3/2009 | Sato | |
| 2009/0076534 A1 | 3/2009 | Shelton et al. | |
| 2009/0287092 A1* | 11/2009 | Leo | A61B 90/06 |
| | | | 385/12 |
| 2010/0058583 A1 | 3/2010 | Cros et al. | |
| 2011/0088435 A1 | 4/2011 | Niarfeix et al. | |
| 2011/0107842 A1 | 5/2011 | Dargahi et al. | |
| 2011/0174862 A1 | 7/2011 | Shelton et al. | |
| 2011/0245865 A1 | 10/2011 | Harper et al. | |
| 2011/0295295 A1 | 12/2011 | Shelton et al. | |
| 2012/0180575 A1 | 7/2012 | Sakano et al. | |
| 2013/0193188 A1 | 8/2013 | Shelton et al. | |
| 2013/0274712 A1 | 10/2013 | Schecter | |
| 2014/0012299 A1* | 1/2014 | Stoddard | A61B 17/320092 |
| | | | 606/169 |
| 2014/0067123 A1 | 3/2014 | Park et al. | |
| 2014/0114327 A1* | 4/2014 | Boudreaux | A61B 34/25 |
| | | | 606/130 |
| 2015/0327914 A1 | 11/2015 | McKenna et al. | |
| 2016/0030240 A1 | 2/2016 | Gonenc et al. | |
| 2016/0066909 A1 | 3/2016 | Baber et al. | |
| 2016/0066916 A1 | 3/2016 | Overmyer et al. | |
| 2016/0074039 A1 | 3/2016 | Beetel | |
| 2016/0089175 A1 | 3/2016 | Hibner et al. | |
| 2017/0143441 A1 | 5/2017 | Paul et al. | |
| 2017/0224280 A1 | 8/2017 | Bozkurt et al. | |
| 2017/0238991 A1 | 8/2017 | Worrell et al. | |
| 2017/0296177 A1 | 10/2017 | Harris | |
| 2017/0296178 A1 | 10/2017 | Miller et al. | |
| 2017/0296179 A1 | 10/2017 | Shelton, IV | |
| 2017/0296180 A1 | 10/2017 | Harris | |
| 2017/0296183 A1 | 10/2017 | Shelton, IV | |
| 2017/0354468 A1 | 12/2017 | Johnson et al. | |
| 2018/0049820 A1 | 2/2018 | Widenhouse et al. | |
| 2018/0049821 A1 | 2/2018 | Shelton, IV et al. | |
| 2018/0073942 A1 | 3/2018 | Wu et al. | |
| 2018/0126504 A1 | 5/2018 | Shelton et al. | |
| 2018/0360446 A1 | 12/2018 | Shelton, IV | |
| 2018/0360454 A1 | 12/2018 | Shelton, IV | |
| 2018/0360473 A1 | 12/2018 | Shelton, IV | |
| 2019/0000446 A1 | 1/2019 | Shelton et al. | |
| 2019/0000448 A1 | 1/2019 | Shelton et al. | |
| 2019/0000478 A1 | 1/2019 | Messerly | |
| 2019/0059928 A1 | 2/2019 | Nicolaescu et al. | |
| 2019/0189898 A1 | 6/2019 | Sieber et al. | |
| 2019/0200863 A1 | 7/2019 | Shelton et al. | |
| 2019/0200985 A1 | 7/2019 | Shelton, IV et al. | |
| 2019/0200987 A1* | 7/2019 | Shelton, IV | A61B 90/98 |
| 2019/0201020 A1 | 7/2019 | Shelton et al. | |
| 2019/0201044 A1 | 7/2019 | Shelton, IV et al. | |
| 2019/0201146 A1 | 7/2019 | Shelton et al. | |
| 2019/0336228 A1 | 11/2019 | Blumenkranz et al. | |
| 2020/0015877 A1* | 1/2020 | Hubelbank | H03H 7/0115 |
| 2020/0222111 A1 | 7/2020 | Yates et al. | |
| 2020/0237372 A1 | 7/2020 | Park | |
| 2020/0245873 A1* | 8/2020 | Frank | A61B 5/0823 |
| 2020/0352639 A1* | 11/2020 | Batchelor | A61B 18/1233 |
| 2020/0367984 A1 | 11/2020 | Peine et al. | |
| 2021/0153928 A1* | 5/2021 | Lennartz | A61B 34/25 |
| 2021/0169559 A1 | 6/2021 | Li et al. | |
| 2021/0212746 A1 | 7/2021 | Shadduck | |
| 2021/0295990 A1 | 9/2021 | Joseph et al. | |
| 2022/0192733 A1* | 6/2022 | Koett | A61B 18/1445 |
| 2022/0370117 A1 | 11/2022 | Messerly et al. | |
| 2023/0000359 A1 | 1/2023 | Saadat et al. | |

FOREIGN PATENT DOCUMENTS

| | | |
|---|---|---|
| EP | 3406205 A1 | 11/2018 |
| EP | 3505105 A1 | 7/2019 |
| KR | 10-20140080488 A | 6/2014 |

OTHER PUBLICATIONS

"Small Temperature Sensor Chip Powers Itself Using Radio Waves," eTeknix, retrieved from the Internet <https://www.eteknix.com/small-temperature-sensor-chip-powers-using-radio-waves/>, 2015, 4 pages.

Covidien, "Covidien SCD396 Sonicision Cordless Ultrasonic Dissection Device, 6 per Case," Tiger Medical, retrieved from the Internet <https://www.tigermedical.com/Products/Sonicision-Cordless-Ultrasonic-Dissection-Device-6-per-Case_COVSCD396.aspx>, 2021, 1 page.

"Enseal X1 Large Jaw Tissue Sealer," retrieved from the Internet <https://https://www.jnjmedicaldevices.com/en-US/product/enseal-x1-large-jaw-tissue-sealer?utm_source=google&utm_medium=cpc&utm_campaign=ethicon-US%2B2021%2Benseal-branded%3BS%3BMD%3BBR%3BSUR%3BHCP%3BBR&utm_content=General&utm_term=%2Benseal&gclid=EAlalQobChMIwOmxI9vH8wIVRbKGCh2qtAmyEAAYASAAEgLu3PD_BwE&gclsrc=aw.ds>, Sep. 2019, 8 pages.

Olympus Medical Systems Europe and MEA, "Thunderbeat Open Extended Jaw—Advanced Open Surgery," retrieved from the Internet <https://www.youtube.com/watch?v=08isvo_VW7s>, Dec. 1, 2014.

Partial European Search Report and Search Opinion received for EP Application No. 22883050.1, mailed on Jul. 21, 2025, 15 pages.

Supplementary European Search Report received for EP Patent Application No. 22883050.1, mailed Nov. 7, 2025, 18 pages.

Chen et al., "Texture Differentiation Using Audio Signal Analysis With Robotic Interventional Instruments;" retrieved online: https://doi.org/10.1016/j.compbiomed.2019.103370-XP085802278,I SSN: 0010-4825; journal homepage: www.elsevier.com/locate/compbiomed Computers in Biology and Medicine vol. 112 (2019) 103370; Jul. 26, 2019; pp. 1-13.

* cited by examiner

INTEGRATED SENSORS FOR ENERGY TOOLS

TECHNICAL FIELD

This disclosure relates generally to the field of robotic surgery and, more particularly, to energy devices, systems and methods for detecting tissue characteristics to help improve the energy application process.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools, for example a surgical stapler and/or an energy device, and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator.

SUMMARY

Aspects of the disclosure include energy tools having integrated sensors and architectures that provide information to the user (e.g., a surgeon) that can be used during the application of energy using an energy tool or device by the surgeon. An "energy tool" or "energy device" as used herein is intended to refer to any surgical instrument that can be used to manipulate a tissue by applying energy during a surgical procedure. For example, an energy tool or device may be any surgical instrument that can emit an energy sufficient to cut, dissect, burn, seal, coagulate, desiccate, fulgurate and/or achieve homeostasis of the tissue upon contact with the tissue. The energy tool or device may apply energy in the form of high frequencies, radio frequencies, ultrasonic waves, microwaves, or the like. The information may be transmitted in real-time wirelessly to a display for the surgeon and/or streamed onto various platforms for use in control systems or machine learning algorithms as a supplemental data source to artificial intelligence and digital surgery. Currently, energy tools are used based on a surgeon's experience and manual control. It is therefore difficult, and mostly dependent on the experience of the surgeon, to determine if the tissue has been optimally grasped, cut, sealed, etc. using the energy tool. For example, uneven or over heating of the tissue with unbalanced or insufficient clamping force may lead to unsuccessful sealing. These aspects may be hard to perceive manually to the surgeon. The instant disclosure therefore proposes to solve this challenge by locating sensors and actuators on the energy tool (without interfering with the energy application functionality of the tool) to quantify/monitor characteristics of the procedure in real time and inform the operator. For example, the characteristics detected by the sensors may include compression force, temperature and/or tissue properties that the operator can then use to help guide the operation such that overheating, char formation and thermal spread are prevented, and the desired thermal effect (e.g., cutting, coagulation, desiccation or fulguration) is achieved.

Representatively, a seal attempt using an energy tool can fail due to impurities (foreign objects or stiff structures) inside the clamped tissue, thermal damage to the tissue, local thermal spread, and/or charring on the blades. In addition, in some aspects, there may be four main effects that energy tools can be used for: cutting, coagulation, desiccation and fulguration. The improper use of energy tools may increase patient morbidity and mortality. Achieving the desired effect requires specific temperatures and is currently done by manually controlling the energy delivery (duty cycle of the tool). This can be quite challenging and relies highly on the technical skill level of the surgeon and the knowledge about the devices. Also, since the tissue is grasped, the tissue is hidden between the graspers of the instrument leaving minimal visual cues to the operator to control energy activation to generate the desired effect.

These challenges are addressed in the instant disclosure by integrating sensors within the energy tool that can be used to monitor the clamping pressure distribution (e.g., via force sensors), monitor the temperature distribution (e.g., via temperature sensors), and monitor the hydration of tissue (e.g., via a microphone) and cease energy activation at the right time. In addition, the sensors are integrated within the energy tool such that they do not interfere with energy application of the bipolar grasping tools, provide continuous accurate data in the presence of fluids in/around the jaws and/or high heat application, can withstand the sterilization cycle, and so the data can be, in some aspects, transmittable wirelessly (e.g., over Bluetooth). In some aspects, the data may be transmitted to a processing component where it is analyzed and then output to a user to help guide them through the procedure. In some aspects, the information may be provided to the user on a display associated with the surgical robotic system, while in other aspects the information may be provided in the form of an alert which indicates to a user, for example, whether or not they should proceed with the energy application.

Representatively, in one aspect the disclosure is directed to an energy tool for a surgical robotic system, the energy tool including a jaw coupled to a base, the jaw having a first anvil that moves relative to a second anvil between an open position and a closed position; and at least one of a force sensor, a temperature sensor and an acoustic sensor coupled to the jaw. In some aspects, the force sensor is a capacitive sensor mounted to the first anvil or the second anvil. In further aspects, the force sensor is a first capacitive sensor coupled to a distal end of the jaw and the energy tool further comprises a second capacitive sensor coupled to a proximal end of the jaw. The force sensor may include a plurality of discrete sensing pads coupled to the jaw. In some aspects, the force sensor may be operable to measure at least one of a total clamping force of the jaw or a concentration point of applied force along the jaw. The temperature sensor may include an analog temperature sensor or a digital temperature sensor coupled to the jaw. In some aspects, the temperature sensor may be operable to monitor a temperature distribution along the jaw. The acoustic sensor may include a micro-electromechanical system microphone coupled to the jaw. In some aspects, the acoustic sensor may include an array of microphones coupled to the jaw. The acoustic sensor may be operable to monitor a hydration level of a tissue during the energy application. In still further aspects, tool may include the force sensor, the temperature sensor and the acoustic sensor, and information detected by the force sensor, the temperature sensor and the acoustic sensor may be analyzed by one or more processors coupled to the energy tool to determine whether a clamping pressure distribution, a temperature distribution and a tissue hydration are suitable for proceeding with the energy application.

In another aspect, a surgical robotic energy tool system is provided including an energy tool having a jaw coupled to a base, the jaw having a first anvil that moves relative to a second anvil between an open position and a closed position during an energy application by the energy tool; one or more sensors configured to detect at least one of a force, a temperature and a tissue phase during the energy application; and one or more processors configured to analyze the detected at least one of the force, the temperature and the tissue phase to provide information for optimizing the energy application. The one or more sensors may include at least two force sensors that each detect a force and provide a force value, and wherein the provided information comprises (1) a total clamping force of the jaw or (2) a concentration point of the clamping force along the jaw. In some aspects, based on the total clamping force of the jaw, the one or more processors further determine an optimal energy application. In some aspects, based on the concentration point of the clamping force, the one or more processors further determine whether an impurity is present in the tissue. In still further aspects, the one or more sensors may include a temperature sensor, and the provided information comprises a temperature distribution along the jaw. The temperature distribution along the jaw may be used to (1) correct a thermal drift in a force sensor, (2) build a heat distribution map along the jaw to be displayed to a user, (3) determine a state of a tissue grasped by the jaw, or (4) modulate energy activation. In still further aspects, the one or more sensors comprises a microphone, and the provided information comprises a hydration level of a tissue grasped by the jaw. In some aspects, based on the hydration level of the tissue, the one or more processors further determine whether the tissue grasped by the jaw is sealed. The system may further display the provided information to a user.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

Figure 1:
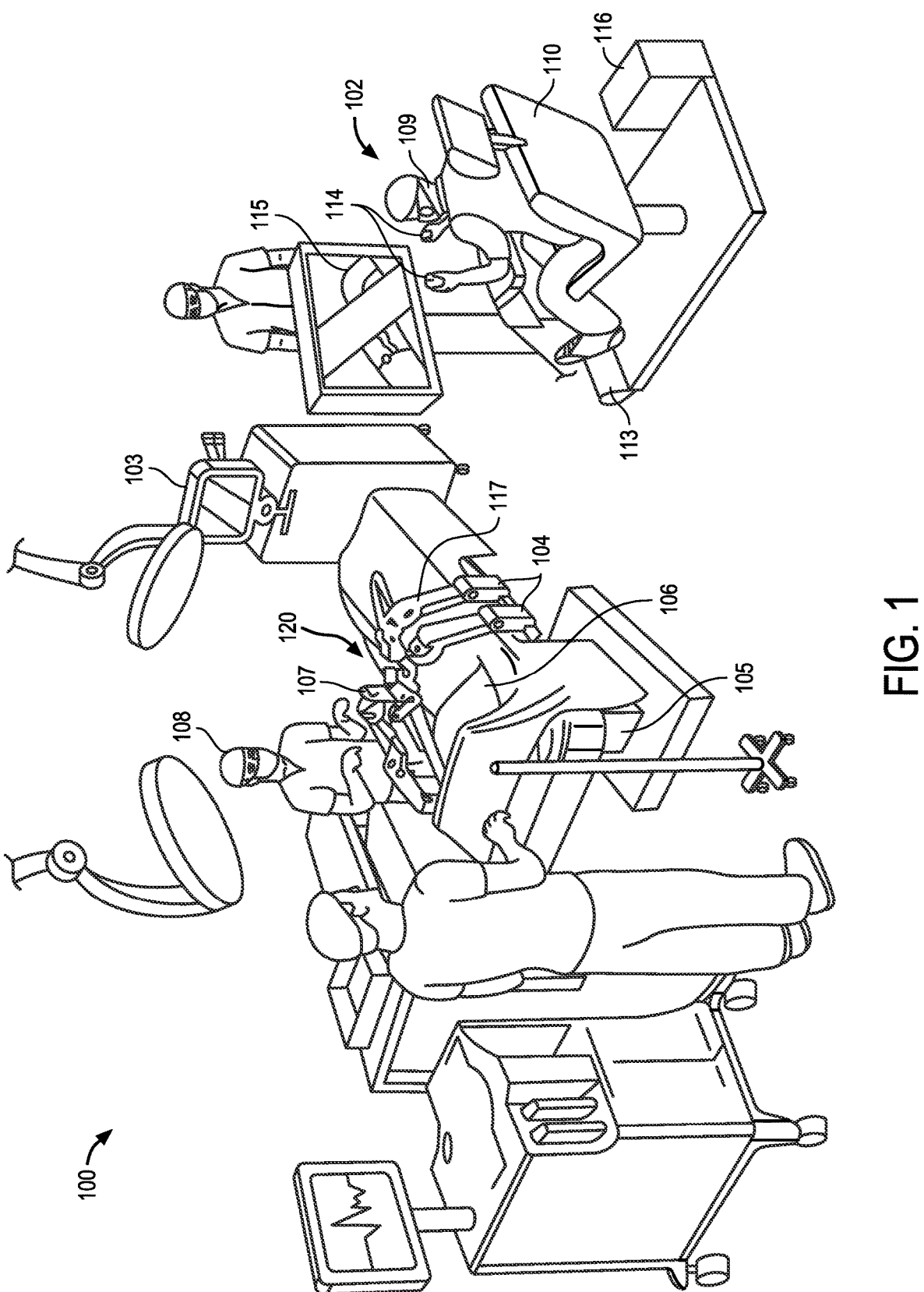
FIG. 1 is an overview schematic of an operating room arrangement with a surgical robotic system.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 may be a grasper that can grasp tissue of the patient and/or an energy tool that can emit energy to cut, coagulate, desiccate and/or fulgurate the grasped tissue. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. Teleoperation may be engaged or disengaged based on the user actions. It should be understood that "engaging" the teleoperation mode is intended to refer to an operation in which, for example, a UID or foot pedal that is prevented from controlling the surgical instrument, is transitioned to a mode (e.g., a teleoperation mode) in which it can now control the surgical instrument. On the other hand, disengaging the teleoperation mode is intended to refer to an operation which occurs when the system is in a teleoperation mode, and then transitioned to a mode (non-teleoperation mode) in which the UID or foot pedal can no longer control the surgical instrument. For example, teleoperation mode may be disengaged when the system determines that a detected movement is an unintended action or movement by the user or the user engages in any other action which suggests teleoperation mode should no longer be engaged.

The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site). To create a port for enabling introduction of a surgical instrument into the patient 106, a trocar assembly may be at least partially inserted into the patient through an incision or entry point in the patient (e.g., in the abdominal wall). The trocar assembly may include a cannula or trocar, an obturator, and/or a seal. In some variations, the trocar assembly can include an obturator such as a needle with a sharpened tip for penetrating through a patient's skin. The obturator may be disposed within the lumen of the cannula when being inserted into the patient 106, and then removed from the cannula such that a surgical instrument may be inserted through the lumen of the cannula. Once positioned within the body of the patient 106, the cannula may provide a channel for accessing a body cavity or other site within the patient 106, for example, such that one or more surgical instruments or tools (e.g., an energy tool) can be inserted into a body cavity of the patient 106, as described further herein. It will be understood that the cannula as described herein may be part of a trocar, and can optionally include an obturator or other components.

Once access is completed, initial positioning or preparation of the robotic system 100 including its arms 104 may be performed. Next, the surgery proceeds with the remote operator 109 at the user console 102 utilising the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilisation and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106. In some aspects, the surgical tool grasper may be a surgical stapler or energy tool and the UIDs 114 are used to control the opening or closing of the jaw of the surgical stapler or energy tool as well as the release of staples and/or energy application through the tissue. When the user is finished controlling the surgical tools with the UIDs 114, the user may dock (i.e., store) the UIDs 114 with docking stations or UID holders located on the console 102.

In some aspects, the communication between the platform 105 and the user console 102 may be through a control tower

103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

Figure 2:
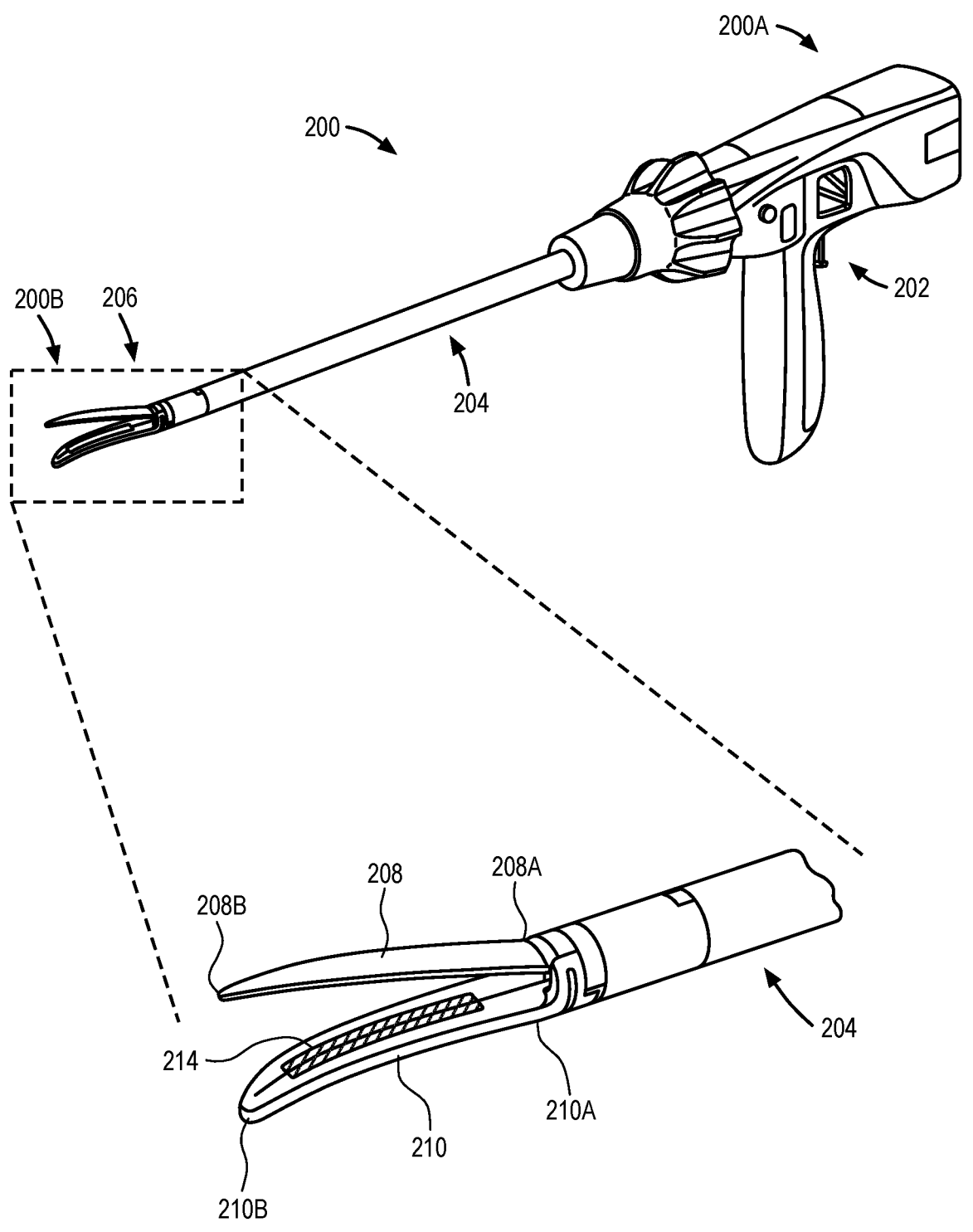
FIG. 2 is a perspective side view of one aspect of an energy tool of a surgical robotic system.

Turning now to FIG. 2, FIG. 2 illustrates a perspective view of one exemplary surgical tool or instrument, in this instance, an energy tool 200 for a surgical robotic system. Energy tool 200 may include a proximal end 200A that is held by the user outside of the patient during a surgical procedure and a distal end 200B that is inserted into the patient during a surgical procedure. Tool 200 may include a handle portion 202, a shaft portion 204 and a jaw 206 coupled to the shaft portion 204. The handle portion 202 may include various mechanisms suitable for manipulating the jaw 206 within the patient and controlling an energy application. The shaft portion 204 may be an elongated portion that connects the handle portion 202 to the jaw 206. The shaft portion 204 may enclose circuitry or other components running from the handle portion 202 to jaw 206 for controlling the jaw 206 and the application of energy. The shaft portion 204 may be used to insert and position the jaw 206 within the patient.

As can be seen from the exploded view of jaw 206, jaw 206 includes a first anvil 208 and a second anvil 210. First anvil 208 may have a proximal end 208A coupled to the shaft portion 204 and a distal end 208B that is a free end distal to the proximal end 208A. First anvil 208 may be movably coupled to shaft portion 204 at a pivot point (e.g., a pivot joint) near the proximal end 208A such that first anvil 208 moves relative to second anvil 210 between an open position (as shown) and a closed position. Similarly, second anvil 210 may have a proximal end 210A coupled to shaft portion 204 and a distal end 210B that is a free end distal to the proximal end 210A. In some aspects, second anvil 210 may be fixedly coupled to shaft portion 204 at the proximal end 210A such that it is a relatively rigid and fixed part of the tool 200. One or both of first anvil 208 and second anvil 210 may include an energy emitting component that emits or applies energy to a tissue clamped or grasped between second anvil 210 and first anvil 208. Representatively, during a surgical procedure, the surgeon inserts jaw 206 into the patient until the desired surgical site is reached. The surgeon then manipulates jaw 206 between the open position and the closed position to clamp onto the tissue at the desired surgical site. The actuator (e.g., trigger) at the handle portion 202 is then used by the surgeon to emit energy from tool 200 and into the clamped tissue.

As previously discussed, tool 200 further includes one or more of a sensor 214 integrated therein. One or more sensors 214 may be mounted to the first anvil 208 and/or second anvil 210. It is contemplated that any number of sensors 214, at any number of positions along tool 200, may be used. Representatively, the one or more sensor 214 may include a single sensor, or may include an array of sensors at different positions along first anvil 208 and/or second anvil 210. In some aspects, the one or more sensors 214 may include one or more of a force or pressure sensor, temperature sensor and/or an acoustic sensor. For example, the force sensor may be a capacitive sensor, or one or more strain gauge sensors. Other types of sensors suitable for obtaining the desired force and/or pressure information are, however, contemplated. The temperature sensor may be a suitable analog or digital sensor compatible with the operating temperatures of the tool 200. The acoustic sensor may be a transducer, for example an acoustic to electric transducer such as a microphone, a micro-electromechanical system (MEMS) microphone or the like.

The information obtained from the sensors 214 may be analyzed by one or more processors associated with the tool 200 and used to optimize energy application of the energy tool 200. This information may, in turn, be displayed (e.g., on display 115) or otherwise communicated or provided to the surgeon (e.g., wirelessly). The surgeon may use this information to, for example, quantify/monitor tissue compression force, temperature and tissue properties in real time to inform the operator and help guide the operation such that overheating, char formation and thermal spread are prevented, and the desired thermal effect (e.g., cutting, coagulation, desiccation or fulguration) is achieved.

Figure 3:
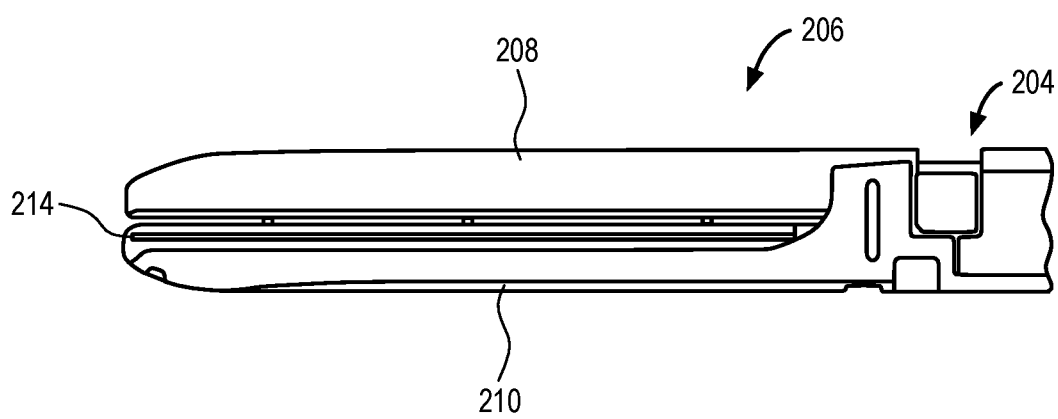
FIG. 3 is a side perspective view of another aspect of an energy tool of a surgical robotic system.
Figure 4:
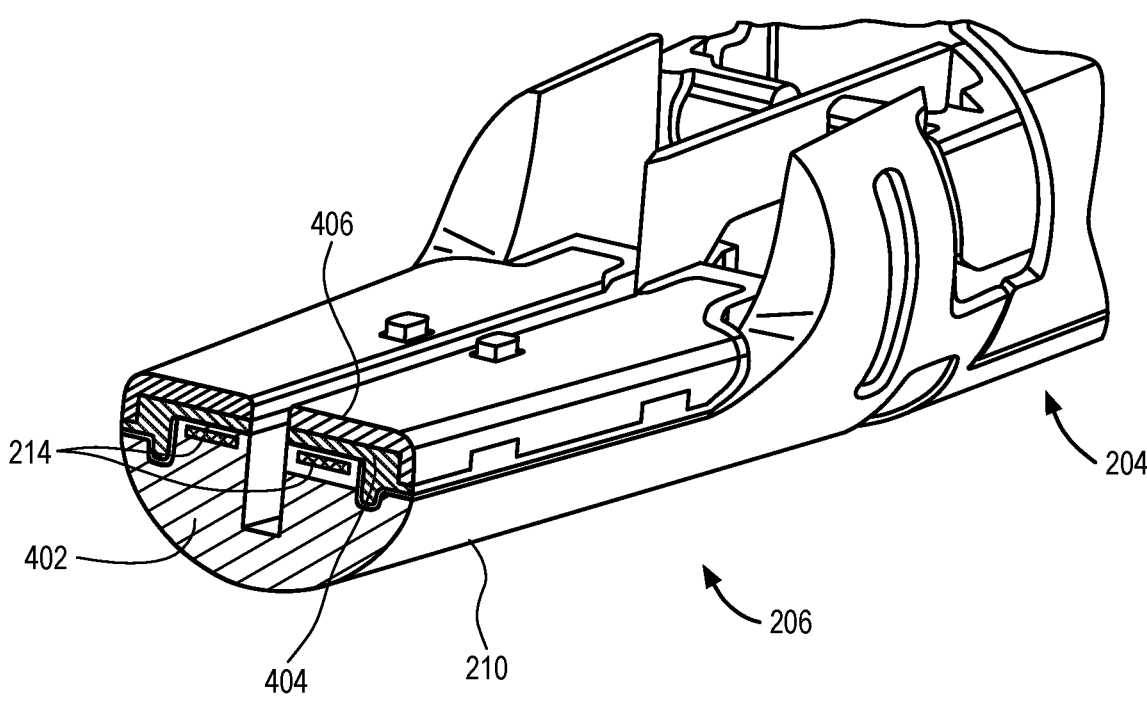
FIG. 4 is a side perspective view of another aspect of an energy tool of a surgical robotic system.
Figure 5:
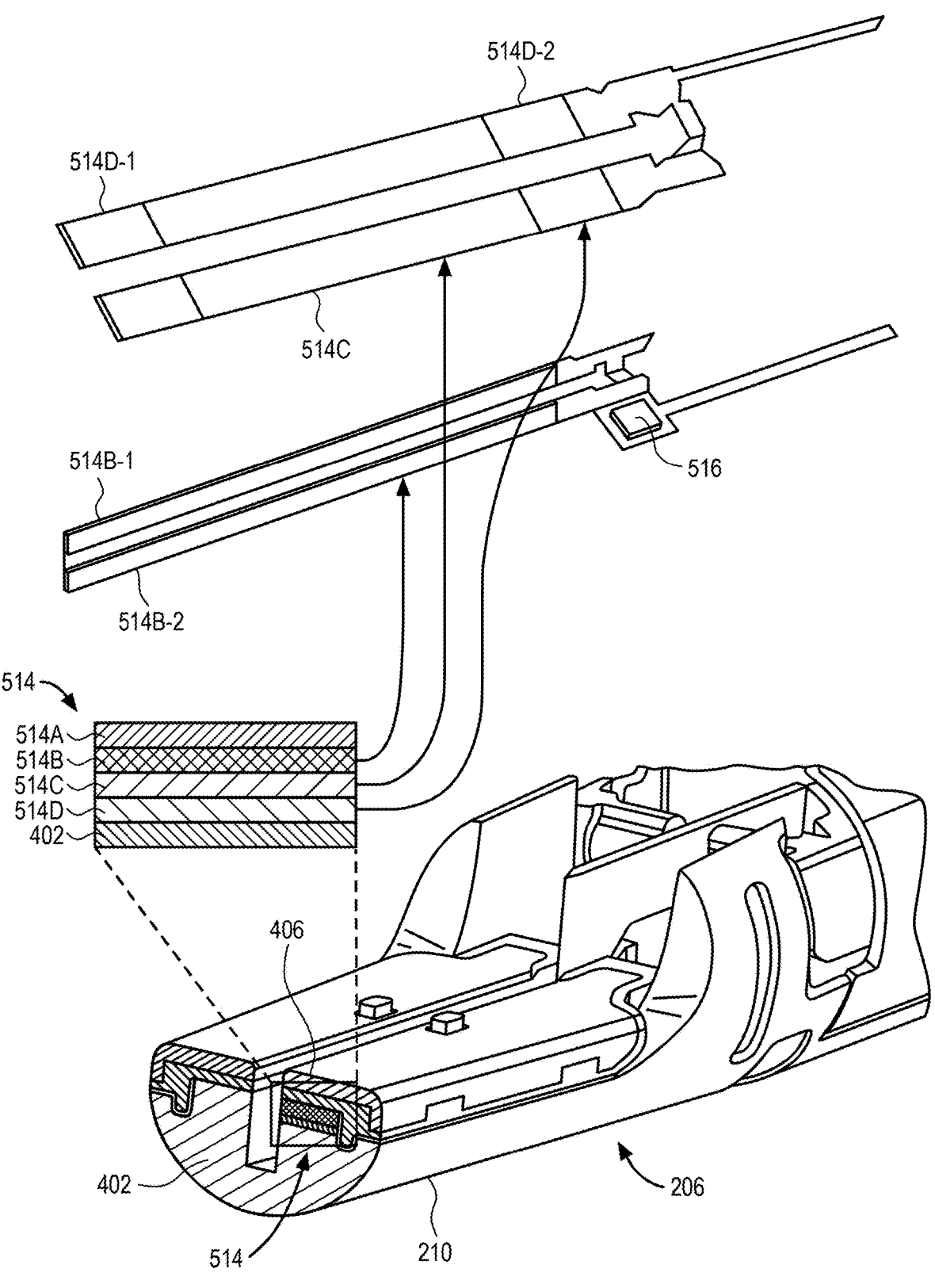
FIG. 5 is an exploded view of another aspect of an energy tool of a surgical robotic system.

A number of representative energy tool and sensor configurations will now be discussed in more detail in reference to FIGS. 3-12. Representatively, FIG. 3, FIG. 4 and FIG. 5 illustrate perspective views of an energy tool jaw having sensors integrated therein. Referring now to FIG. 3, FIG. 3 illustrates a side perspective view of jaw 206 including first anvil 208 and second anvil 210. From this view, it can be seen that the one or more sensors 214 are integrated into second anvil 210. In some aspects, the one or more sensors 214 may extend along a substantial portion of second anvil 210 such that different measurements (e.g., corresponding to a pressure, force, temperature or sound) can be taken along the jaw 206.

Referring now in more detail to the sensor configuration, FIG. 4 illustrates the one or more sensors 214 embedded within jaw 206. Representatively, jaw 206 may include a jaw body 402, an insulating layer 404 formed on the jaw body, and an energy layer 406 formed on the insulator layer 404. The jaw body 402 may be formed by a metal, and may be, or may be a portion of, the second anvil 210 forming jaw 206. The insulator layer 404 may be any type of electrically insulating layer suitable for use in an energy tool. The energy layer 406 may be any type of energy layer suitable for emitting or applying energy to a tissue positioned within jaw 206. As can further be seen from this view, in one aspect, the one or more sensors 214 are positioned or embedded between jaw body 402 and insulator layer 404. For example, in this aspect, the one or more sensors 214 may include, but are not limited to, capacitive sensor pads positioned underneath the insulator layer 404 of jaw 206. In one aspect, the capacitive sensor pads may form a thin pad layer inside second anvil 210 and be used for measuring (1) the total clamping force, and (2) the concentration point of the applied force along the graspers. In some aspects, at least a pair of capacitive pads, which are connected by the metal jaw body 402 from underneath and by the insulating boundary of the jaw insulator layer 404 from above, may be used. Therefore, the capacitive sensing pads are isolated from the current flowing during the energy application of the energy layer 406 to minimize interference to the sensor readouts. In some aspects, a number of capacitive pads can be arranged in an array and cover the entire jaw body 402 surface area to get a pressure distribution map. In some aspects, to measure the total grasping force and compute an overall force concentration point along jaw 206, at least two capacitive sensor pads, one at the proximal end 210A and one at the distal end 210B, may be used as will be described in more detail in reference to FIGS. 8-9.

Figure 6:
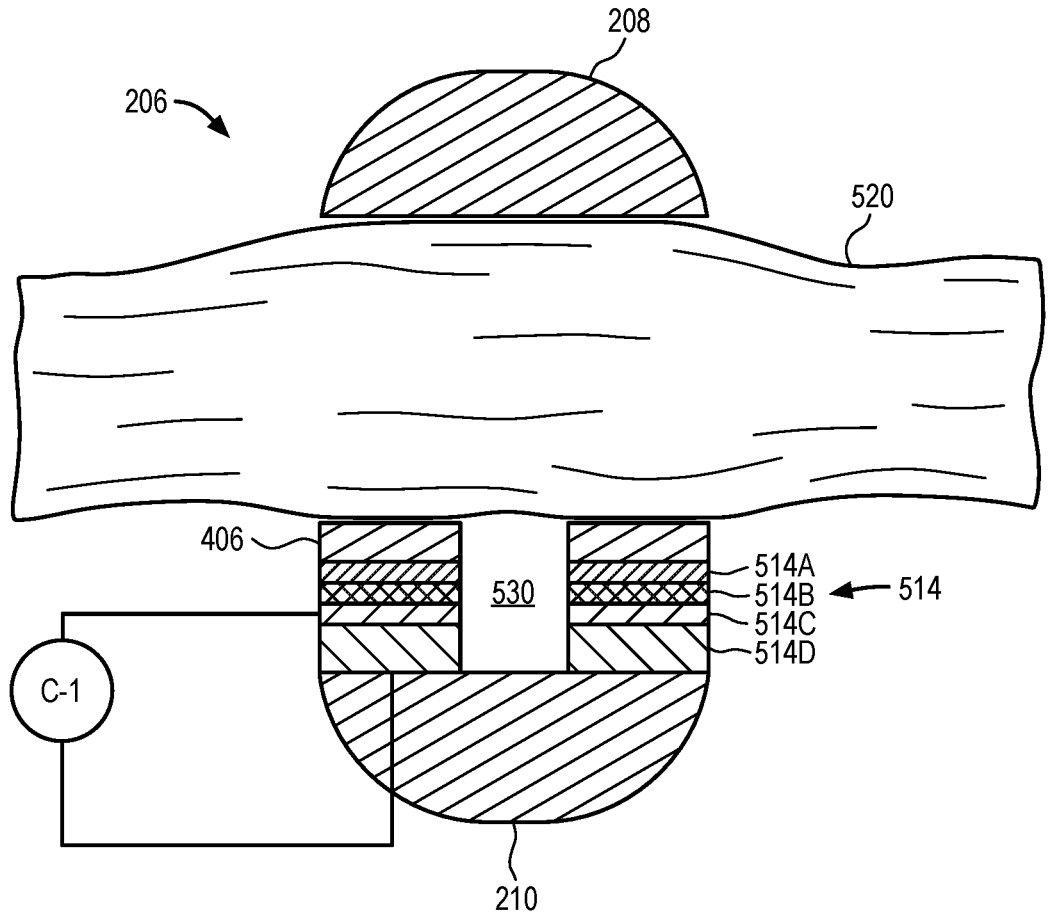
FIG. 6 is an end cross-sectional view of another aspect of an energy tool of a surgical robotic system.
Figure 7:
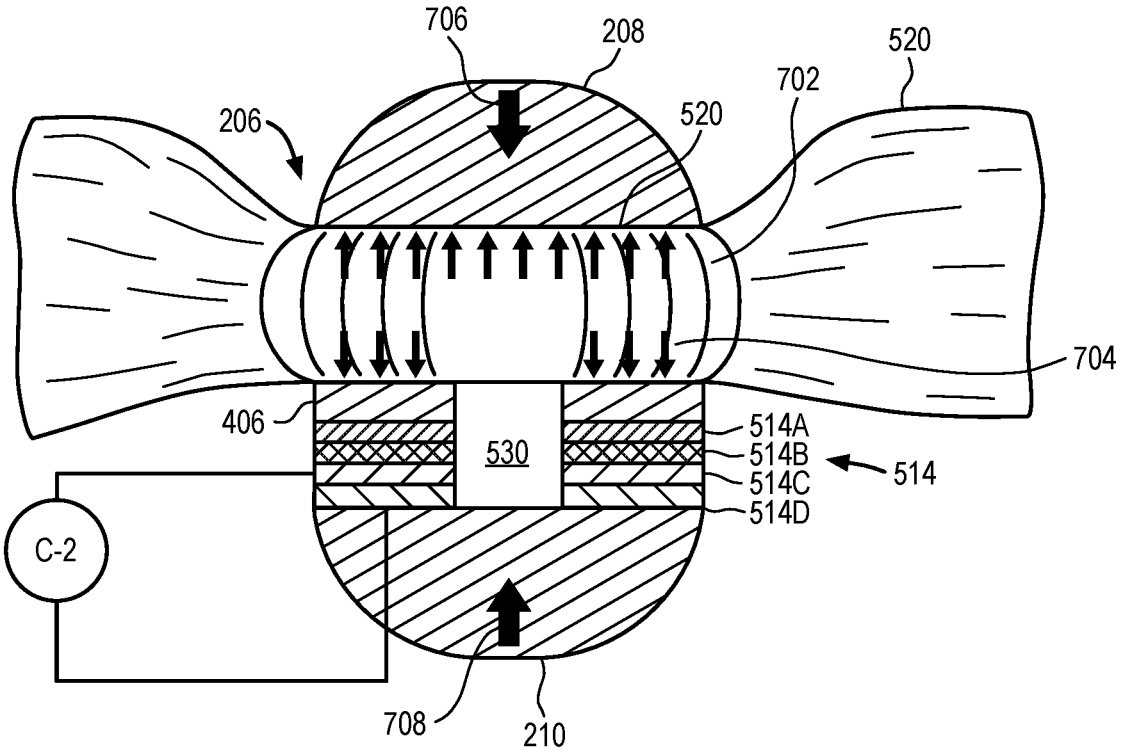
FIG. 7 is an end cross-sectional view of another aspect of an energy tool of a surgical robotic system.

Referring now to FIG. 5, FIG. 6 and FIG. 7, FIG. 5 illustrates an exploded perspective view of one representative sensor, and FIG. 6 and FIG. 7 illustrate cross-sectional end views of the sensor, integrated into an energy tool. More specifically, FIG. 5 illustrates a force sensor 514 integrated into second anvil 210 of jaw 206. Referring now in more detail to force sensor 514 embedded within second anvil 210, force sensor 514 may be a multi-layered structure. The multi-layered structure may be made up of an insulator layer 514A, a top metal sheet 514B, a flex circuit 514C, and a capacitive pad including a dielectric elastomer 514D. The insulator layer 514A may be the insulator layer 404 of the jaw 206 as previously discussed. Top metal sheet 514A may be coupled to the insulator layer 514B, and acts as the deforming electrode of the sensor when forces are applied. The flex circuit 514C including the capacitive pads and electro-mechanically responsive dielectric elastomer 514D act as the sensing medium. As can be seen from the exploded view of sensor top metal sheet 514B, top metal sheet 514B may be an elongated two pronged structure including metal sheets 514B-1 and 514B-2. As can further be seen from the exploded view, flex circuit 514C is a similarly shaped two pronged structure with discrete capacitive pads and dielectric elastomer 514D-1 and 514D-2 structures coupled thereto. The dielectric elastomer is coupled to the metal jaw body 402, which then acts as the fixed electrode of the capacitive sensor 514. The top side of the flex circuit 514C contacting the insulator 514A (e.g., the insulator 404 of the jaw 206) includes the metal sheets 514B-1 and 514B-2 of the deforming electrode 514B of the sensor and a chip 516 for actively monitoring the capacitance level. The assembly may further include a 3 Volt power supply and I2C bus to power and transmit data through wires running along the tool shaft (e.g., tool shaft 204) to a wireless data transmission (Bluetooth) module located on the tool handle (e.g., tool handle 202).

FIG. 6 and FIG. 7 illustrate cross-sectional end views of the force sensor 514 described in reference to FIG. 5, during operation. Representatively, FIG. 6 shows a tissue 520 positioned between first anvil 208 and second anvil 210 of jaw 206 before tool activation. In addition, as can further be seen from this view, in some aspects, second anvil 210 may include a gap 530 that may be dimensioned to accommodate a central cutting blade (not shown). FIG. 6 shows jaw 206 in a relatively open position around tissue 520. In other words, the tissue 520 is positioned between anvils 208, 210, but anvils 208, 210 are not compressing the tissue to any detectable degree. In this open configuration, the capacitive pads and electro-mechanically responsive dielectric elastomer 514D of sensor 514 are shown in a resting or un-deformed configuration. In this configuration, capacitive pads and electro-mechanically responsive dielectric elastomer 514D may be considered as having a first capacitance (C-1). FIG. 7 shows tissue 520 being compressed between the first and second anvils 208, 210 during tool activation. From this view, it can be seen that during tool activation, one or both of first and second anvils 208, 210 move toward one another as illustrated by arrows 706, 708 to compress the tissue 520 and energy may be applied. The tissue compression force is illustrated by arrows 704. In addition, current 702 is shown flowing through tissue 520. The tissue compression force is illustrated by arrows 704. The tissue compression, further causes capacitive pads and electro-mechanically responsive dielectric elastomer 514D of sensor 514 to be deformed (e.g., compress) as shown. This decrease in the gap between metal sheet/deforming electrode 514B and the jaw body 402 (e.g., the fixed electrode) may be detected as a rise in capacitance or a second capacitance (C-2). The previously discussed chip 516 may actively monitor the capacitance level and/or changes in capacitance levels and the detected information may be transmitted to the wireless data transmission (Bluetooth) module located on the tool handle and analyzed to determine, for example, total clamping force and/or a concentration point of the applied force along the jaw. This information may, in turn, be displayed or otherwise communicated to the user (e.g., an alert) to help guide operation of the tool.

In some aspects, a sensing algorithm may be used by one or more processors associated with the energy tool 200 for analyzing the force or pressure information obtained by the force sensor(s) 514. A representative sensing algorithm that may be used will now be described in detail in reference to FIGS. 8-9 and the following formulas. Representatively, after identifying the force at each sensor location, their summation will give the total compressive force on the tissue and the concentration point of the force can be computed using the following Formulas (1) and (2):

$$F_{tissue} = F1 + F2$$

$$X_{tissue} = L1 + (F2/(F1 + F2))*L2$$

Representatively, the summation of the forces F1 and F2 will provide the total tissue clamping force (Ftissue) as shown by the following Formula (1):

$$F_{tissue} = F1 + F2$$

The center of application of the force may be determined as shown by the following Formula (2):

$$X_{tissue} = L1 + (F2/(F1 + F2))*L2$$

Figure 8:
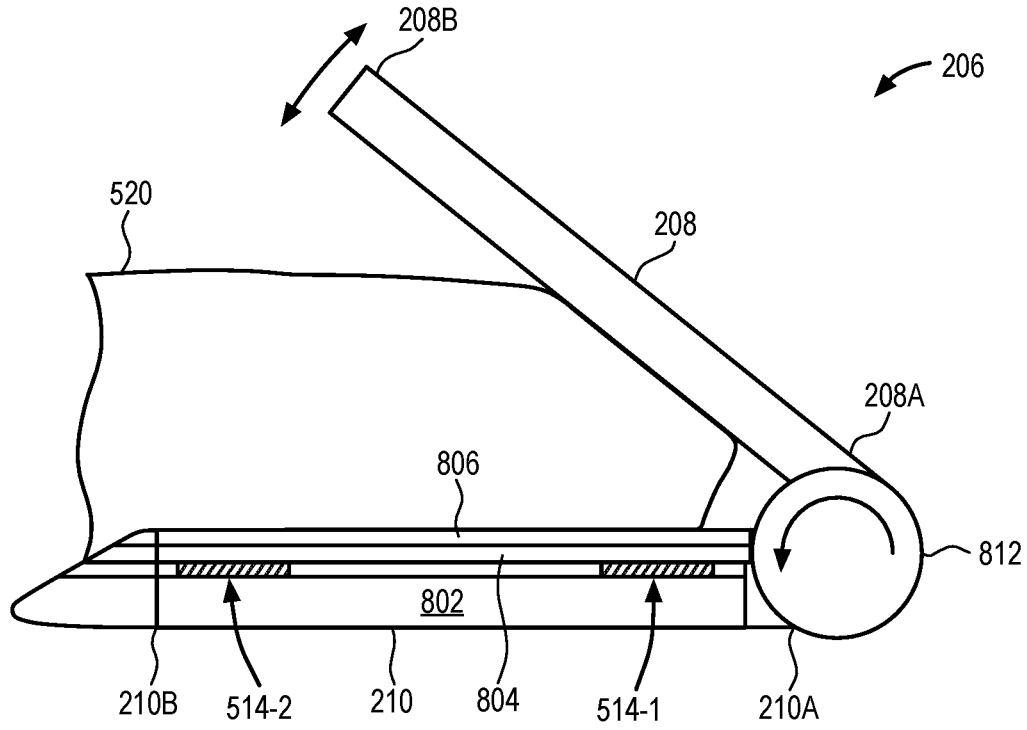
FIG. 8 is a cross-sectional side view of another aspect of an energy tool of a surgical robotic system.
Figure 9:
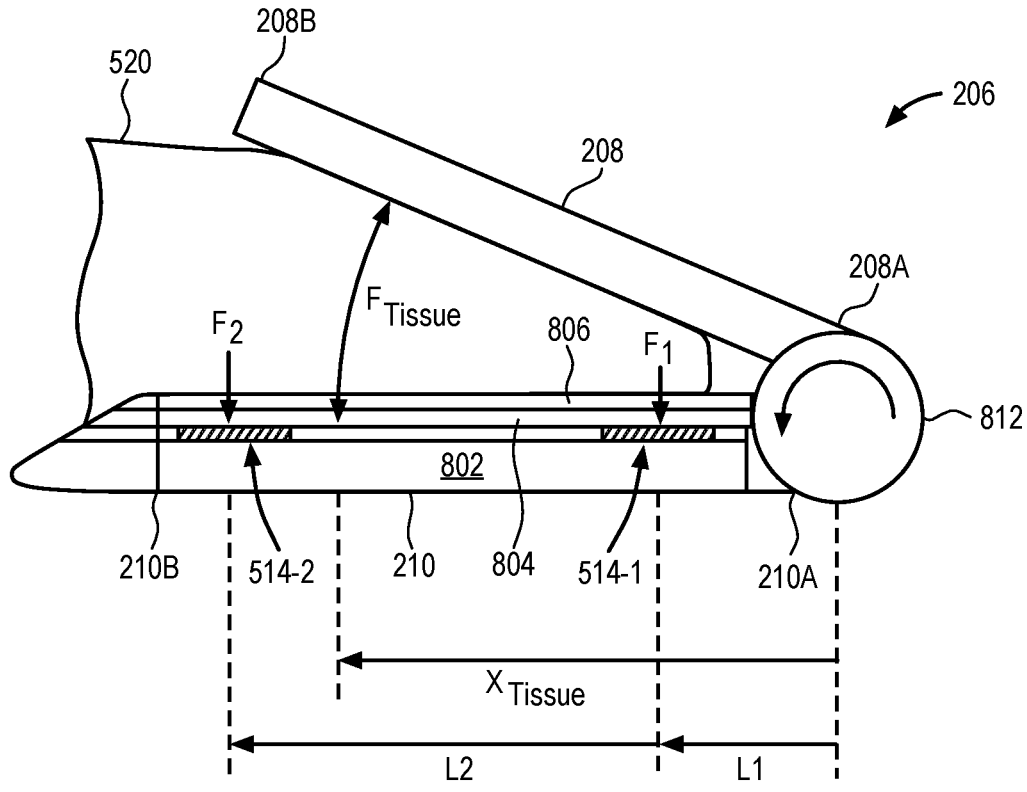
FIG. 9 is a cross-sectional side view of another aspect of an energy tool of a surgical robotic system.

Representatively, as illustrated by FIG. 8 and FIG. 9, which illustrate cross-sectional side views of an energy tool having sensors integrated therein. The energy tool jaw 206 may be the same jaw previously discussed in reference to FIG. 2 and include a first anvil 208 and a second anvil 210. From this view, it can be seen that the first anvil 208 rotates (or otherwise moves) relative to second anvil 210 about pivot joint 812 between an open position (shown) and a closed position. The second anvil 210 may include a body portion 802, insulating layer 804 and energy layer 806. The body portion 802, insulating layer 804 and energy layer 806 may be substantially the same as the body portion 402, insulating layer 204 and energy layer 406 previously discussed in reference to FIG. 2. A tissue 520 is further shown positioned within jaw 206 between first anvil 208 and second anvil 210. Thus, the application of energy from jaw 206 will go through tissue 520 held within jaw 206 to produce the desired thermal effect on the tissue (e.g., cutting, coagulation, desiccation, fulguration or the like).

From this view, it can further be seen that at least two force sensors 514-1 and 514-2 are integrated into second anvil 210. Sensors 514-1, 514-2 may, for example, be force sensors that detect a force or pressure on second anvil 210 when jaw 206 clamps onto tissue 520. Representatively, sensors 514-1, 514-2 may be capacitive force sensors. Sensors 514-1, 514-2 may be mounted between the insulating layer 804 and body portion 802 such that the body portion 802 of second anvil 210 makes up the fixed electrode of the sensor, as previously discussed. Sensors 514-1, 514-2 may consist of multi-layered structures as previously discussed in reference to FIGS. 5-7. When first anvil 208 is moved relative to second anvil 210 from the open position (FIG. 8) to a closed position (FIG. 9) the pressure from the tissue 520 compressed therein is detected by sensors 514-1, 514-2 and, based on this information, a corresponding tissue force (Ftissue) can be determined.

For example, sensors 514-1, 514-2 may be integrated into second anvil 210 at different known positions or locations so that different pressure and/or force readings can be detected and used to determine information and/or a characteristic associated with the energy application operation so that it can be optimized. For example, the sensors may measure or detect information that can be used to determine the clamping force, it's center of application, clamping force profile/variation along the jaw and/or stiffness of the clamped tissue layer. This characteristic or information may, in turn, be displayed to the surgeon and used to determine whether conditions are suitable for energy application to proceed and/or how to optimize the energy application to achieve the desired result. In still further aspects, the energy operation may be automatically prevented depending on the detected information. Representatively, sensor 514-1 may be mounted at a known position or location near the proximal end 210A of second anvil 210. Sensor 514-2 may be mounted at a known position or location near the distal end 210B of second anvil 210. In this aspect, pressure or force readings at two different known locations along the second anvil 210 are detected. The two force readings from sensors 514-1, 514-2 may then be analyzed to determine a total grasping force of the jaw and/or force application center location. This information can, in turn, be used by the surgeon to help identify the tissue they are grasping onto with the stapler 200 and help guide energy application.

For example, referring now to FIG. 9, the force value (F1) determined from sensor 514-1 and the force value (F2) determined from sensor 514-2 are added together to obtain the total clamping force (Ftissue) as shown by Formula (1). In addition, the location (L1) of sensor 514-1 at the proximal end (e.g., base capacitive sensor) is known and location (L2) of the sensor 514-2 at the distal end (e.g., tip capacitive sensor) is also known. If the moment at the same rotation point (hinge between anvil and base) is used, and the sensor geometry is known, the center of application of the force (Xtissue) can then be determined using the previously discussed Formula (2). This information may be displayed to the surgeon and the surgeon may use this information to determine whether energy application should proceed, should continue to proceed and/or how to optimization the energy application to achieve the desired result (e.g, tissue sealing). For example, the surgeon may determine based on this information that tissue 520 is not centered, for example, tissue 520 is closer to the distal end than the proximal end, and whether or not at this position, the application of energy will produce the desired thermal effect on the tissue 520.

In addition, it should be understood that during the energy application cycle, the temperature of the jaw 206 will increase significantly. This could lead to a drift in capacitance measurements from each force sensor 514. In order to avoid this, the drift of each capacitive sensor may be modeled with respect to a neighboring temperature sensor measurement, or a neighboring capacitive pad can be added with a proper protective shield to capture only the influence of the temperature with no effect of the grasping force. Then the detected drift of the neighbor capacitive pad can be used for the thermal correction of the actual force-sensing capacitive pads. After the temperature correction, the capacitance change of each sensor can be converted into a force value by multiplying with a calibration constant. The calibration constant can be determined through an experimental calibration by applying a known load on each sensor and measuring/modeling the resulting capacitance change on each sensor. After identifying the force at each sensor location, their summation will give the total compressive force (Ftissue) on the tissue as previously discussed. In addition, using a torque balance equation (e.g., Formula 2), the concentration point of the force (Xtissue) can be computed as previously discussed.

Figure 10:
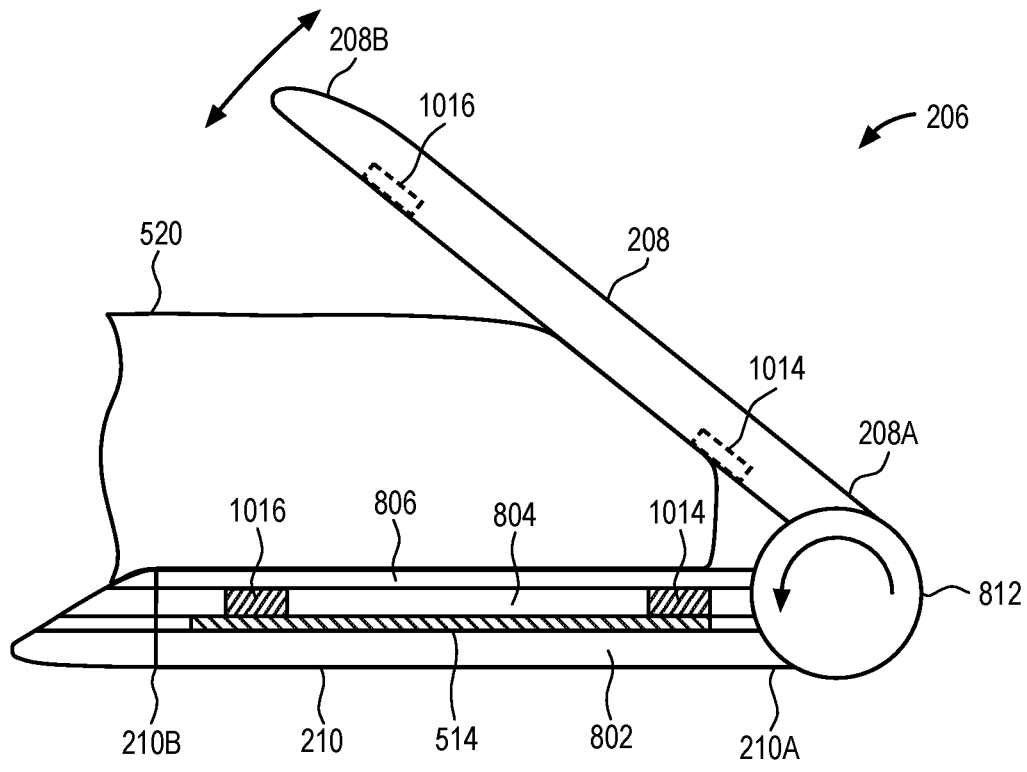
FIG. 10 is a cross-sectional side view of another aspect of an energy tool of a surgical robotic system.

Referring now to FIG. 10, FIG. 10 illustrates a cross-sectional side view of the sensor including each of a force sensor, temperature sensor and acoustic sensor integrated into the energy tool. Representatively, from this view, it can be seen that the energy tool (e.g., energy tool 200) may include a force sensor 514 as previously discussed, as well as at least one or more of a temperature sensor 1014 and an acoustic sensor 1016 integrated into jaw 206. The temperature sensor 1014 and/or the acoustic sensor 1016 may be integrated into first anvil 208 and/or second anvil 210 of jaw 206. Representatively, in one aspect, temperature sensor 1014 and/or acoustic sensor 1016 may be embedded within the insulating layer 804 of second anvil 210. In other aspects, it is contemplated that temperature sensor 1014 and/or acoustic sensor 1016 may be mounted to first anvil 208.

Figure 11:
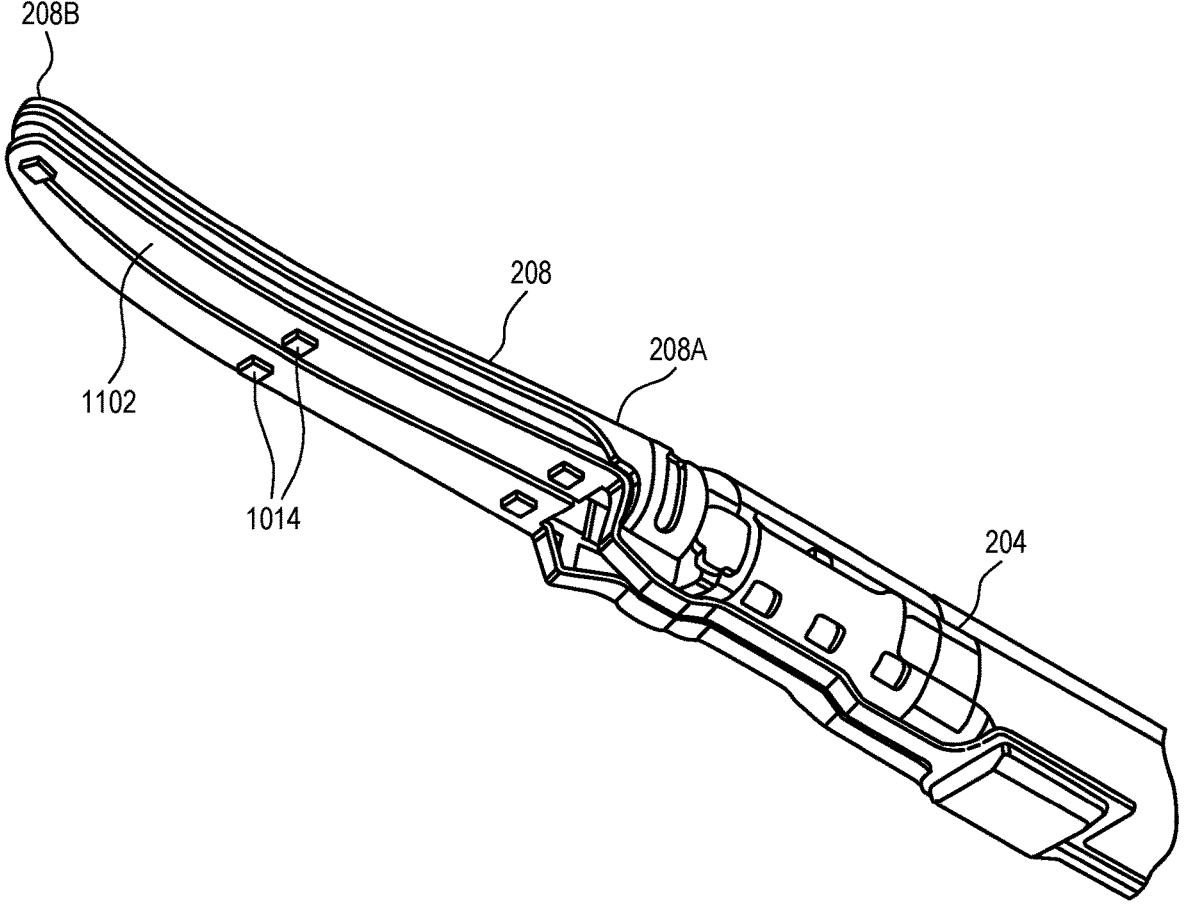
FIG. 11 is a side perspective view of another aspect of an energy tool of a surgical robotic system.

Referring now in more detail to temperature sensor 1014, temperature sensor 1014 may monitor a temperature distribution along the jaw 206. In one aspect, temperature sensor 1014 may be a standard analog or digital temperature sensor that is compatible with the operating temperatures of the energy tool. As illustrated by FIG. 10, temperature sensor 1014 can be embedded inside the insulating layer 804 of the second anvil 210 of jaw 206. As illustrated by FIG. 11, in other aspects, temperature sensor 1014 can be coupled to an independent flex circuit 1102 mounted inside first anvil 208. One or more of temperature sensors 1014 may be coupled to flex circuit 1102. Readings of the sensor(s) can be transmitted via a common 2 wires I2C bus, which can be a shared line with any one or more of the other sensors, and the information may then be used for energy tool optimization.

Representatively, by way of background, tissue necrosis and hemostasis by heating using an energy tool follows a specific temperature pattern. The process of denaturation of tissue begins with the irreversible aggregation of macromolecules and the unraveling of collagen helices around 60 degrees Celsius (C). Protein denaturation occurs between 70 degrees Celsius and 80 degrees Celsius resulting in coagulation. Further heating to 90 degrees Celsius results in dehydration or desiccation. Beyond 100 degrees Celsius, the intercellular water boils, eventually vaporizing the cell allowing tissue cutting. Finally, tissue fulguration or carbonization occurs beyond 200 degrees Celsius. The continual local temperature data provided by the one or more temperature sensors 1014 can therefore be used to not only eliminate/correct the thermal drift in force sensors as previously discussed, but to also build a heat distribution map along the jaw and display the information to the operator as intra-operative feedback and/or predict the local state of the grasped tissue and track the progression of different phases (denaturation at 60° C., coagulation at 70-80° C., desiccation at 90° C., cutting at and above 100° C., and fulguration beyond 200° C.). In addition, the information from the temperature sensors 1014 can be used to generate warnings or modulate energy activation (adjust duty cycles) to control temperature, prevent thermal damage to the tissue, and ensure the desired effect is generated (cutting, coagulation, desiccation or fulguration). It should further be appreciated that the integration of the temperature sensors 1014 in the energy tool provides direct temperature measurements of the jaw, which is more accurate than an indirect measurement which may be subject to inaccuracies and therefore limited due to, for example, variations in tissue (type and thickness). Furthermore, the heat distribution map provides an accurate temperature gradient map throughout the entire jaw surface, as opposed to only a single temperature value, that can be used to guide the energy tool.

Referring now to the acoustic sensor 1016, acoustic sensor may be used to monitor the hydration level of the tissue and, in turn, the tissue phase during the energy application. As the tissue goes through different modes with the increasing temperature level, its hydration level decreases due to rapid vaporization. The sound of the water bursting up through the tissue makes a sizzling sound, which may be detected by acoustic sensor 1016 embedded inside the tissue grasping interface of the tool (e.g., embedded within and/or above the insulating layer 804 of second anvil 210). In some aspects, acoustic sensor 1016 may be a micro-electromechanical system (MEMS) microphone or other similarly sized microphone suitable for integration within jaw 206. Representatively, in some aspects acoustic sensor 1016 may be a MEMS microphone having a size of approximately 700 square microns, or a microphone having a size of about 3.5 millimeters×2.7 millimeters. The acoustic sensor 1016 should further have proper protection from the elevated temperatures of the tool's tissue grasping surface and liquid (e.g., an elastic cover on the sound port). In addition, in some aspects, acoustic sensor 1016 may include an array of microphones coupled to jaw 206 as previously discussed, which can be used to monitor the tissue condition throughout the jaw interface. The microphone(s) can, for instance, detect when the rapid evaporation process has ended and thus signal a proper time to discontinue energy application when desiccation is the desired effect without transitioning to the next phase of burning the tissue.

Figure 12:
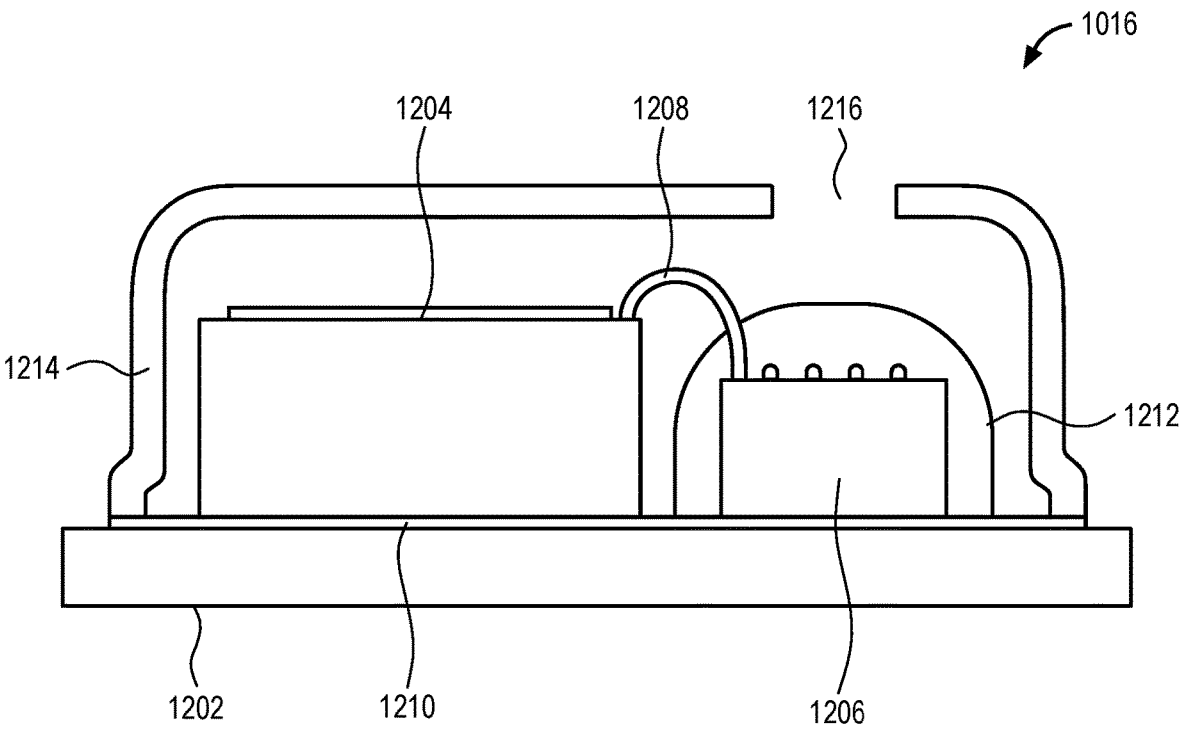
FIG. 12 is a cross-sectional side view of another aspect of a sensor of an energy tool of a surgical robotic system.

One representative acoustic sensor 1016 is illustrated in FIG. 12. In particular, as can be seen from FIG. 12, in one aspect, acoustic sensor 1016 may include a printed circuit board (PCB) 1202 having a MEMS transducer 1204 (e.g., MEMS microphone) coupled thereto, for example by seal 1210. An application-specific integrated circuit (ASIC) 1206 may further be coupled to PCB 1202 and MEMS transducer 1204 by wire 1208. Each of the sensor components may further be encased within enclosure 1214 having a sound port 1216 to allow for sound to pass to the MEMS transducer 1204. In addition, in some aspects, a glob top molding 1212 may be provided over ASIC 1206 to protect ASIC 1206 from elevated temperatures and/or liquids. One or more of the sensor assemblies illustrated in FIG. 12 may be embedded within the first anvil 208 or the second anvil 210 of jaw 206 as previously discussed. It should further be understood that although one representative sensor assembly is illustrated, it is contemplated that other assembly configurations may be used therefore sensor assembly 1016 is not limited to what is shown in FIG. 12.

Figure 13:
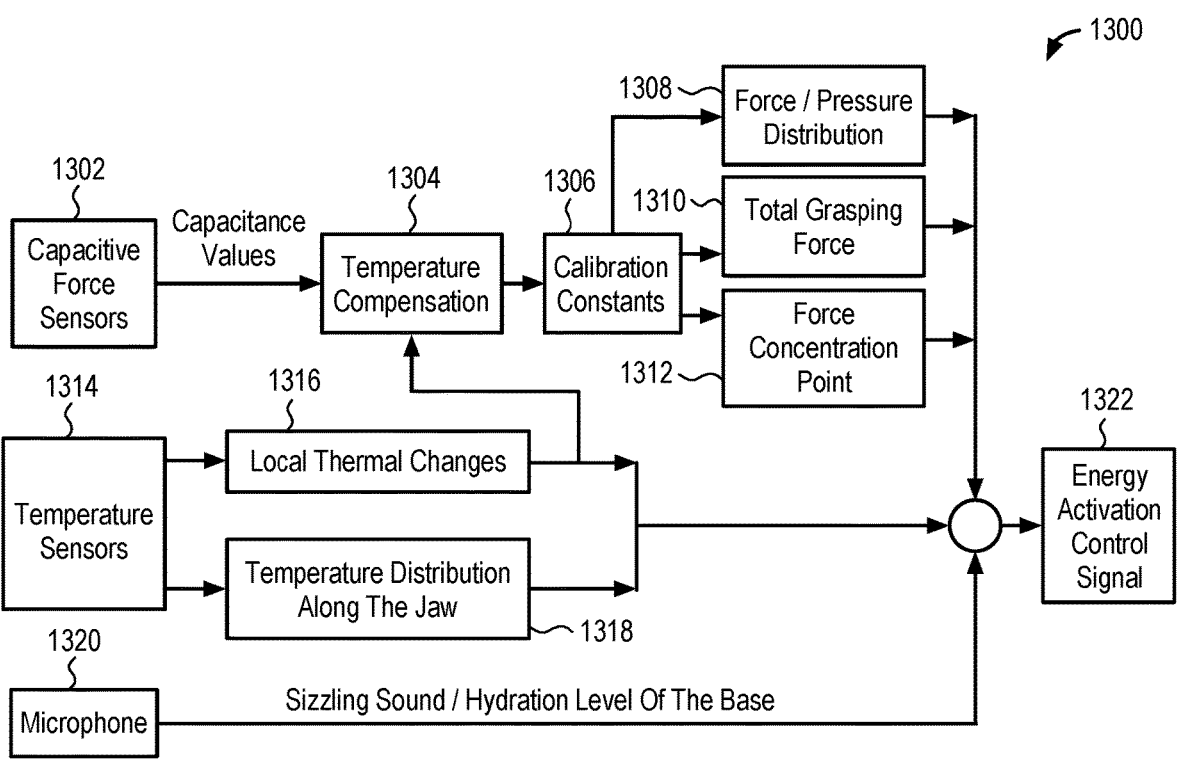
FIG. 13 is a block diaphragm of a processing operation for an energy tool of a surgical robotic system.

Referring now in more detail to the control strategy, FIG. 13 illustrates one representative control algorithm or strategy for analyzing and using the information detected by the sensors to operate the energy tool. As previously discussed, the force sensor(s) (e.g., sensors 514) may be used to measure the compressive force applied by the tool jaw (e.g., energy tool jaw 206). This force should be above a certain threshold to ensure proper tissue sealing. Due to the capacitive nature of the force sensor, however, it could be affected by the temperature changes of jaw 206. The temperature sensor 1014 or another capacitive sensor that captures only the thermal drift effect without any influence from the applied grasping force, may therefore further be provided to correct the impact of the temperature changes on the other sensors. The temperature sensor 1014 may be a single sensor, or may be an array of temperature sensors that can detect temperature distributions along the jaw 206 of tool 200. Depending on the desired effect on the tissue (cutting, coagulation, desiccation and/or fulguration), the temperature and the duty cycle of energy activation can be modulated.

Representatively, in one aspect, the cutting effect may be achieved by using a continuous waveform (100% duty cycle) applied through the active electrode of the energy tool 200. In some aspects, energy tool 200 may have a narrow tip that allows for large current concentration and when placed near the tissue but not in contact, generates an arc through which the current rushes to the tissue generating large amount of heat (greater than 100° C.) which leads to rapid tissue vaporization and induces cutting. When a blunt instrument tip is used with contact on the tissue, the decreased current concentration due to increased surface area leads to increase in the tissue temperature but not to the point of vaporization and creates a coagulum at temperatures between 70 to 80° C. and desiccation at a temperature of 90° C. To perform coagulation or desiccation, a lower duty cycle high voltage waveform is used but can also be performed with 100% duty cycle lower voltage cutting waveform as well. In fulguration, a lower duty cycle high voltage waveform is applied through the active electrode of a pointed monopolar electrosurgical tool tip in non-contact mode close to the tissue. With high voltage and low duty cycle (usually 6%), the heat generated by the current flowing through the arc from the tool tip heats the tissues to form coagulum and with repeated application, increases the temperate to 200° C. or more forming carbonization or fulguration. The acoustic sensor 1016 can further sense sizzling of the tissue and hydration content of the tissue. For robotic tools, the optimal jaw closure force can also be incorporated into the control theory of the tool for more precise tissue sealing.

Referring now in more detail to process 1300, in one aspect, process 1300 includes detecting force or capacitance values at operation 1302 using the force sensors (e.g. force sensors 514). As previously discussed, the detected force or capacitance values may be sensitive to temperature drift due to the high temperatures of the energy device. Therefore, in some aspects, a temperature compensation may be performed at operation 1304. Representatively, at operation 1314, one or more of the temperature sensor(s) (e.g., temperature sensors 1014) may detect a temperature at various positions/locations along the jaw to provide both a local temperature reading or output at operation 1316 and a temperature distribution map along the jaw at operation 1318. Based on this information, a temperature compensation can be performed at operation 1304 and calibration constants can be determined at operation 1306 using known calculations. The force and/or capacitance values determined based on these operations can then be used to determine a force/pressure distribution map at operation 1308, a total grasping force at operation 1310 and a force concentration point at operation 1312. Still further, at operation 1320, the acoustic sensor(s) (e.g., acoustic sensor 1016) may be used to detect a sizzling sound and determine a hydration level of the tissue to help the user understand when the tissue has been properly sealed. Based on all of the collected information, the system algorithm and/or the user can determine the energy activation needed to be output to properly seal the tissue and output a corresponding energy activation control signal at operation 1322. For example, using the sensor information, the system may apply filters (or processing algorithms) to identify events, characteristics or quantifiers for the events or characteristics, and using that information, do post-operative analysis or directly inform surgeon about characteristics or information relating to energy application that can be used to guide the surgeon while using the energy tool. In some aspects, the information may be used by the system to automatically adjust or control the energy tool, while in other cases the information may be used by the surgeon to manually adjust or control the tool for optimum performance. In some aspects, there may be portions of the energy application that once the information from the sensor is obtained, the system can use this information to determine optimal operation parameters and automatically control the energy tool. In addition to information from the sensors integrated into the energy tool, the system may also use information from cameras, microphones or other sensors associated with other tools to detect other characteristics that may provide additional context for determining the optimal use and/or output of the energy tool.

In some aspects, one or more of the characteristics such as the force/pressure distribution map, total grasping force, force concentration point, local thermal change, temperature distribution map and/or sizzling sound/hydration level determined at operations 1308, 1310, 1312, 1316, 1318 and/or 1320 may be output or otherwise displayed to the user to help the user during the energy application.

Figure 14:
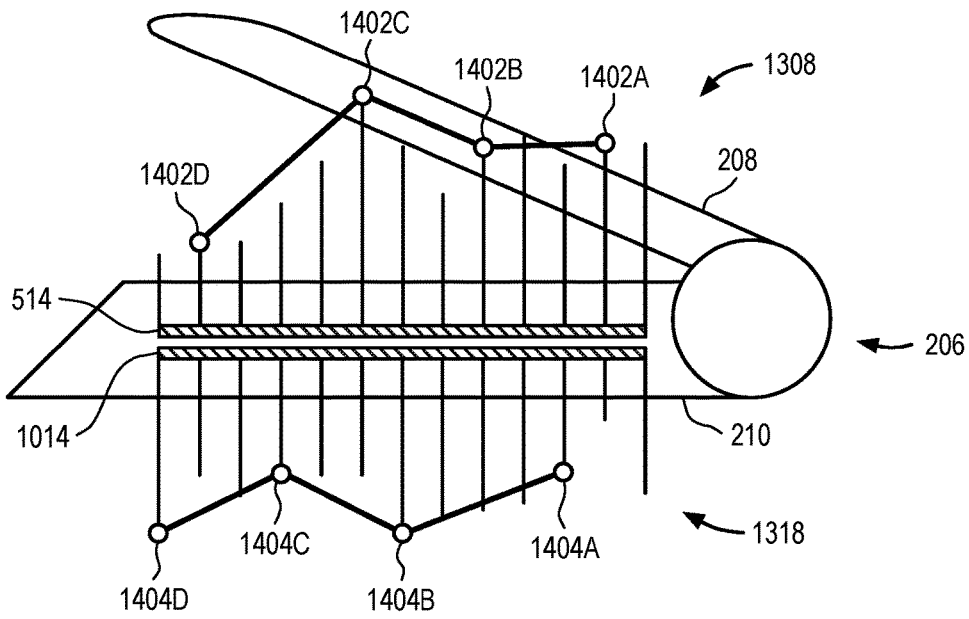
FIG. 14 is a cross-sectional side view of another aspect of an energy tool of a surgical robotic system.

FIG. 14 illustrates a representative force/pressure distribution map determined at operation 1308 and temperature distribution map determined at operation 1318 that may be displayed, or otherwise communicated to the user. Representatively, the sensing algorithm and processing operations previously discussed may be used to determine a force or pressure distribution profile along the jaw 206 as illustrated in FIG. 14. Representatively, using Formula (1), localized force measurements (e.g., Ftissue1, Ftissue2, Ftissue3 and Ftissue4) are determined at the locations of different force sensors 514 distributed along jaw 206. Based on these localized force measurements, a force distribution map 1308 along the anvil surface is generated as shown in FIG. 14. The force distribution map 1308 may be displayed to the surgeon and used to monitor a force concentration along the jaw during energy application. Representatively, based on force distribution map 1308, it can be understood that the force concentration at points 1402A, 1402B, 1402C and 1402D vary. For example, the force concentration appears to spike at point 1402C. When a force concentration is found to be higher at one region than another it may be determined by the system, or visually by the user, that that region may include an abnormality or impurity (e.g., tumor, stiff structure or a foreign object). Once an impurity is detected, the system and/or the surgeon may decide that energy application needs to be modified prior to proceeding so that the seal does not fail due to the impurity. The detection of an abnormality or impurity and/or providing the user with a warning regarding the same is helpful in guiding surgeons learning to use the tool, as well as experienced surgeons, in proper use of the energy tool.

Similarly, the sensing algorithm and processing operations previously discussed may be used to determine a temperature distribution profile along the jaw 206 as illustrated in FIG. 14. Representatively, localized temperature measurements may be determined at the locations of different temperature sensors 1014 distributed along jaw 206. Based on these localized temperature measurements, a temperature distribution map 1318 along the anvil surface is generated as shown in FIG. 14. The temperature distribution map 1318 may provide an accurate temperature gradient map throughout the entire jaw surface. The temperature distribution map 1318 may be displayed to the surgeon and used to monitor a temperature concentration along the jaw during energy application. Representatively, based on temperature distribution map 1318, it can be understood that the temperature at points 1404A, 1404B, 1404C and 1404D may be different and varies along the jaw. Knowing the temperature at certain points along the jaw can be used to help eliminate/correct the thermal drift in the force sensors as discussed herein. In addition, the information can help the surgeon understand the local state of the grasped tissue and track the progression of different phases of energy application. For example, based on the different temperatures represented by the temperature distribution map 1318, the surgeon can determine whether the phase is denaturation (e.g., at 60 degrees Celsius), coagulation (e.g., at 70-80 degrees Celsius), desiccation (e.g., at 90 degrees Celsius), cutting at and above 100 degrees Celsius, and/or fulguration (e.g., beyond 200 degrees Celsius). In addition, when the temperature distribution map shows temperatures at portions of the jaw are above certain thresholds, the system may generate warnings prompting a user to modulate energy activation, or automatically modulate energy activation (adjust duty cycles) to control temperature, prevent thermal damage to the tissue, and ensure the desired effect is generated (cutting, coagulation, desiccation or fulguration).

In some aspects, the one or more sensors embedded in the jaw can transmit data through the wires running along the shaft of the instrument to a wireless transmission (Bluetooth) module located inside the tool handle, and/or can be transmitted via a line running together with the energy cables to a central processing unit. After the temperature, force, and microphone data are transmitted to the processing computer, algorithms (can be machine-learning-based) can be run to modulate the duty cycle and energy level to control grasper temperature and keep it at the optimal level while showing valuable information to the surgeon on a display (such as the heat map of the graspers, phase of the tissue heating process or intra-operative suggestions) which can either be overlaid on the surgical view or provided on a separate external screen.

Figure 15:
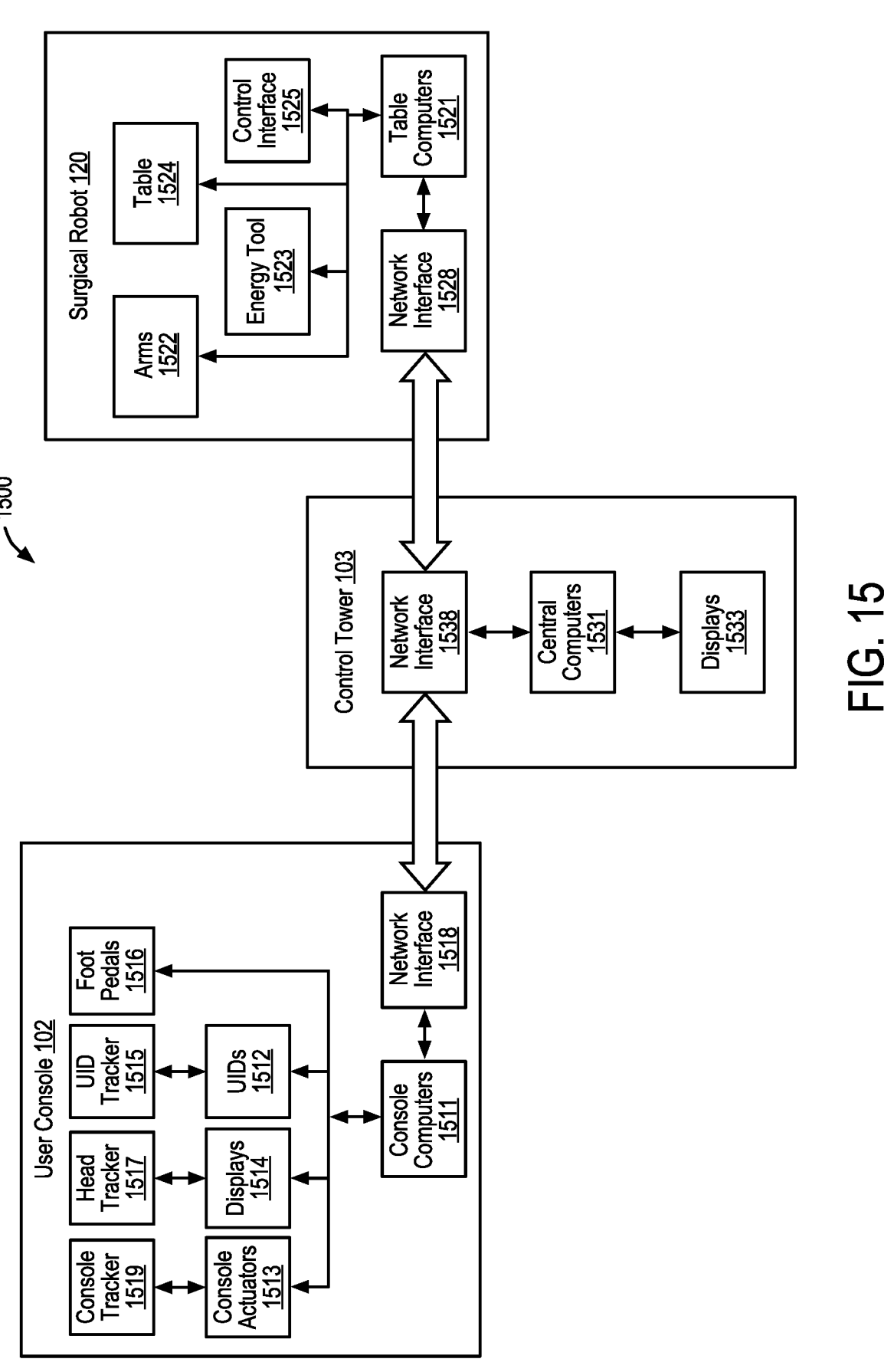
FIG. 15 is a block diagram of a computer portion of a surgical robotic system including an energy tool, in accordance with an aspect of the disclosure.

FIG. 15 is a block diagram of a computer portion of a surgical robotic system, which is operable to implement any one or more of the previously discussed operations. The exemplary surgical robotic system 1500 may include a user console 102, a surgical robot 120, and a control tower 103. The surgical robotic system 1500 may include other or additional hardware components; thus, the diagram is provided by way of example and not a limitation to the system architecture.

As described above, the user console 102 may include console computers 1511, one or more UIDs 1512, console actuators 1513, displays 1514, foot pedals 1516, console computers 1511 and a network interface 1518. In addition, user console 102 may include a number of components, for example, a UID tracker(s) 1515, a display tracker(s) 1517 and a console tracker(s) 1519, for detecting various surgical conditions required for operation of the system (e.g., UID orientation, orientation of the surgeon relative to the display, orientation the console seat, etc). It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 1513 based on user input or stored configurations by the console computers 1511. The user may perform robot-assisted surgeries by controlling the surgical robot 120 using one or more master UIDs 1512 and foot pedals 1516. Positions and orientations of the UIDs 1512 are continuously tracked by the UID tracker 1515, and status changes are recorded by the console computers 1511 as user input and dispatched to the control tower 103 via the network interface 1518. Real-time surgical video of patient anatomy, instrumentation, and relevant software apps can be presented to the user on the high resolution 3D displays 1514 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 15, the control tower 103 may include central computers 1531 including at least a visualization computer, a control computer, and an auxiliary computer, various displays 1533 including a team display and a nurse display, and a network interface 1538 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an operating table 1524 with a plurality of integrated robotic arms 1522 that can be positioned over the target patient anatomy. An energy tool 1523 can be attached to or detached from the distal ends of the arms 1522, enabling the surgeon to perform various surgical procedures. The energy tool 1523 may be any one or more of the energy tools having sensors integrated therein as previously discussed in reference to FIG. 2-FIG. 14. The surgical robot 120 may also comprise control interface 1525 for manual or automated control of the arms 1522, table 1524, and tools 1523. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 1522 includes four arms mounted on both sides of the operating table 1524, with two arms on each side. For certain surgical procedures, an arm mounted on one side of the table can be positioned on the other side of the table by stretching out and crossing over under the table and arms mounted on the other side, resulting in a total of three arms positioned on the same side of the table 1524. The surgical tool can also comprise table computers 1521 and a network interface 1528, which can place the surgical robot 120 in communication with the control tower 103.

The foregoing description, for purposes of explanation, used specific nomenclature to provide a thorough understanding of the invention. However, it will be apparent to one skilled in the art that specific details are not required in order to practice the invention. Thus, the foregoing descriptions of specific aspects of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. An energy tool for a surgical robotic system, the energy tool comprising:

a jaw coupled to a base, the jaw having an anvil that moves relative to a jaw portion between an open position and a closed position; and a temperature sensor and a second sensor comprising a force sensor or an acoustic sensor coupled to the jaw, wherein when the second sensor is the force sensor the temperature sensor is proximal to the force sensor and is configured to detect a temperature of the jaw at various positions along the jaw proximal to the force sensor, and wherein the detected temperature is used to generate a temperature distribution map of along the jaw used to correct a thermal drift of the force sensor and monitor different phases of energy application.

2. The energy tool of claim 1 wherein the force sensor is a capacitive sensor mounted to the anvil or the jaw portion.

3. The energy tool of claim 2 wherein the force sensor is a first capacitive sensor coupled to a distal end of the jaw and the energy tool further comprises a second capacitive sensor coupled to a proximal end of the jaw.

4. The energy tool of claim 2 wherein the force sensor comprises a plurality of discrete sensing pads coupled to the jaw.

5. The energy tool of claim 1 wherein the force sensor is operable to measure at least one of a total clamping force of the jaw or a concentration point of applied force along the jaw.

6. The energy tool of claim 1 wherein the temperature sensor comprises an analog temperature sensor or a digital temperature sensor coupled to the jaw, and the different phases of energy application comprise denaturation, coagulation, desiccation, cutting at and above 100 degrees Celsius, and fulguration.

7. The energy tool of claim 1 wherein a local state of a tissue is further determined based on the detected temperature at various positions, and when the temperature distribution map shows temperatures at portions of the jaw are above predetermined thresholds, energy application is modulated.

8. The energy tool of claim 1 wherein the acoustic sensor comprises a micro-electromechanical system microphone coupled to the jaw.

9. The energy tool of claim 1 wherein the acoustic sensor comprises an array of microphones coupled to the jaw.

10. The energy tool of claim 1 wherein the acoustic sensor is operable to monitor a hydration level of a tissue during an energy application.

11. The energy tool of claim 1 wherein the energy tool comprises the force sensor, the temperature sensor and the acoustic sensor, and information detected by the force sensor, the temperature sensor and the acoustic sensor is analyzed by one or more processors coupled to the energy tool to determine whether a clamping pressure distribution, a temperature distribution and a tissue hydration are suitable for proceeding with an energy application.

* * * * *